(12) United States Patent
Ido et al.

(10) Patent No.: US 10,183,883 B2
(45) Date of Patent: Jan. 22, 2019

(54) METHANE FERMENTATION SYSTEM

(71) Applicants: Koji Ido, Okayama (JP); Yasumasa Ido, Okayama (JP)

(72) Inventors: Koji Ido, Okayama (JP); Yasumasa Ido, Okayama (JP)

( * ) Notice: Subject to any disclaimer, the term of this patent is extended or adjusted under 35 U.S.C. 154(b) by 0 days.

(21) Appl. No.: 15/664,830

(22) Filed: Jul. 31, 2017

(65) Prior Publication Data

US 2017/0327398 A1   Nov. 16, 2017

Related U.S. Application Data

(62) Division of application No. 15/501,282, filed as application No. PCT/JP2015/071645 on Jul. 30, 2015, now Pat. No. 9,957,183.

(30) Foreign Application Priority Data

Aug. 4, 2014 (JP) .................................. 2014-158980

(51) Int. Cl.
  *C12M 1/107*   (2006.01)
  *C02F 11/04*   (2006.01)
  (Continued)

(52) U.S. Cl.
  CPC .............. *C02F 11/04* (2013.01); *B01D 61/02* (2013.01); *B01D 61/14* (2013.01); *B01D 61/145* (2013.01);
  (Continued)

(58) Field of Classification Search
  CPC .......... C02F 11/00; C02F 11/04; B01D 61/02; B01D 61/14; B01D 61/58; C12M 21/04;
  (Continued)

(56) References Cited

U.S. PATENT DOCUMENTS 4,985,149 A * 1/1991 Ohshima .................... C02F 3/28
                                                                 210/603
6,368,849 B1 * 4/2002 Norddahl .............. C02F 3/2853
                                                                 210/603
(Continued)

FOREIGN PATENT DOCUMENTS

JP       H04326994       11/1992
JP       2001170631 A    6/2001
(Continued)

OTHER PUBLICATIONS

International Search Report dated Nov. 10, 2015 issued in corresponding PCT International Application No. PCT/JP2015/071645.
(Continued)

*Primary Examiner* — William H. Beisner
(74) *Attorney, Agent, or Firm* — Troutman Sanders LLP (57) ABSTRACT

A methane fermentation system which can efficiently generate methane gas is provided. The methane fermentation system decomposes an organic waste with an anaerobic microorganism to cause methane fermentation so as to generate the methane gas. The methane fermentation system includes a wet bead mill which finely pulverizes the organic waste. The methane fermentation system also includes a methane fermentation chamber in which the organic waste finely pulverized in the wet bead mill is decomposed with the anaerobic microorganism to cause the methane fermentation so as to generate the methane gas.

5 Claims, 6 Drawing Sheets

(51) Int. Cl.
  *B01D 61/02* (2006.01)
  *B01D 61/14* (2006.01)
  *B01D 61/58* (2006.01)
  *B09B 3/00* (2006.01)
  *C02F 11/00* (2006.01)
  *C12P 5/02* (2006.01)
  *B01D 61/16* (2006.01)
  *C12M 1/26* (2006.01)
  *C12M 1/33* (2006.01)
  *C12M 1/00* (2006.01)
  *C02F 1/44* (2006.01)
  *C02F 3/28* (2006.01)

(52) U.S. Cl.
  CPC ............. *B01D 61/16* (2013.01); *B01D 61/58* (2013.01); *B09B 3/00* (2013.01); *C02F 11/00* (2013.01); *C12M 21/04* (2013.01); *C12M 33/14* (2013.01); *C12M 45/02* (2013.01); *C12M 47/02* (2013.01); *C12P 5/023* (2013.01); *B01D 61/025* (2013.01); *B01D 2311/04* (2013.01); *B01D 2311/08* (2013.01); *B01D 2311/25* (2013.01); *B01D 2317/025* (2013.01); *C02F 1/441* (2013.01); *C02F 1/444* (2013.01); *C02F 3/2853* (2013.01); *C02F 2303/26* (2013.01); *Y02E 50/343* (2013.01)

(58) Field of Classification Search
  CPC ...... C12M 33/14; C12M 45/02; C12M 47/02; C12P 5/023
  See application file for complete search history.

(56) References Cited

U.S. PATENT DOCUMENTS

2011/0281255 A1   11/2011   Rozich
2011/0281341 A1   11/2011   Rozich
2013/0295625 A1   11/2013   Chang et al.

FOREIGN PATENT DOCUMENTS

| | | |
|---|---|---|
| JP | 2003063886 A | 3/2003 |
| JP | 2003088895 A | 3/2003 |
| JP | 2004-230273 A | 8/2004 |
| JP | 2005238103 A | 9/2005 |
| JP | 2006159045 A | 6/2006 |
| JP | 2006239624 A | 9/2006 |
| JP | 2008253870 A | 10/2008 |
| JP | 2010-017615 A | 1/2010 |
| JP | 2010142735 A | 7/2010 |
| JP | 2011230100 A | 11/2011 |
| JP | 2013532051 A | 8/2013 |
| WO | 2011143169 A2 | 11/2011 |

OTHER PUBLICATIONS

Taherzadeh M. et a l. Pretreatment of Lignocellulosic Wastes to Improve Ethanol and Biogas Production: A Review. International JM olecular Sciences 9:1621-1651, 2008.

Lu J. et a l. Simultaneous Pretreatment and Acidogenesis of Solid Food Wastes by a Rotational Orum Fermentation System . . . Bioresource Technology 138:101-108, 2013.

Rieker C. et . la Anaerobic Degradation of Beer Spent Grains for Biogas Production. Brauwelt 132(16/17)716-718, 720-721, 1992.

Chynoweth O. Biomass Conversion Options. Aquatic Plants for Water Treatment and Resource Recovery. 621-642, 1987.

Extended European Search Report dated Jan. 9, 2018 during the prosecution of European Patent Application No. 15829865.3.

European Search Report dated Nov. 9, 2018 during the prosecution of European Patent Application No. 15829865.3.

* cited by examiner

METHANE FERMENTATION SYSTEM

CROSS-REFERENCE TO RELATED APPLICATIONS

This application is a Divisional of U.S. application Ser. No. 15/501,282, filed Feb. 2, 2017. U.S. Ser. No. 15/501,282 is a U.S. national phase application under 35 U.S.C. § 371 of International Patent Application No. PCT/JP2015/071645, filed Jul. 30, 2015, and claims benefit of priority to Japanese Patent Application No. 2014-158980, filed Aug. 4, 2014. The entire contents of these applications are hereby incorporated by reference.

TECHNICAL FIELD

The present invention relates to a methane fermentation method and a methane fermentation system for generating methane gas by decomposing organic substances with an anaerobic microorganism and thereby causing methane fermentation.

BACKGROUND

Conventionally, for example, as a technology for generating methane gas by causing, with an anaerobic microorganism, methane fermentation on organic substances containing a large amount of solid such as food residues, livestock manure and woody raw materials, a system is known that has a configuration in which the organic substances are pulverized or crushed to be sieved into predetermined particle diameters and in which thereafter methane fermentation is caused (for example, see Japanese Laid-open Patent Publication No. 2010-142735).

SUMMARY

However, in the configuration of PLT1 described above, specific means for pulverizing the organic substances and particle diameters after the pulverization are not provided, and even when organic substances are crushed or pulverized with general crushing/pulverizing means, the efficiency of conversion into methane gas is low, with the result that it is impossible to efficiently generate methane gas.

In particular, when organic substances containing a woody or fibrous component are used, it takes much time to decompose the organic substances with an anaerobic microorganism, with the result that it is impossible to efficiently generate methane gas.

The present invention is made in view of the foregoing points, and an object thereof is to provide a methane fermentation method and a methane fermentation system with which it is possible to efficiently generate methane gas.

An example methane fermentation method includes a pulverization step of finely pulverizing an organic substance in a wet bead mill; a methane fermentation step of supplying the organic substance which is finely pulverized in the pulverization step to a methane fermentation chamber and decomposing the organic substance with an anaerobic microorganism to cause methane fermentation so as to generate methane gas; a separation step of separating, with a UF membrane, a digestive fluid after the methane fermentation in the methane fermentation step into a concentrated liquid and a permeation liquid; a return step of returning the concentrated liquid separated in the separation step to the methane fermentation chamber; and an agitation step of agitating contents of the methane fermentation chamber with a water flow produced by the return of the concentrated liquid in the return step.

An example methane fermentation method is configured such that in the methane fermentation method above, the methane fermentation step, the separation step, the return step and the agitation step are repeated.

An example methane fermentation method is configured such that in the pulverization step, the organic substance is finely pulverized in the wet bead mill such that a particle diameter at 50% in a cumulative distribution with respect to a volume is equal to or less than 20 μm.

An example methane fermentation method is configured such that in the pulverization step, a moisture content of the organic substance is adjusted such that a solid content is equal to or less than 10%, and the organic substance is finely pulverized in the wet bead mill.

An example methane fermentation method is configured such that in the pulverization step, the organic substance is finely pulverized in the wet bead mill for one hour or more.

An example methane fermentation method is configured such that in the separation step, the permeation liquid separated with the UF membrane is separated with an RO membrane.

An example methane fermentation method is configured such that before the digestive fluid after the methane fermentation in the methane fermentation step is separated in the separation step, a colony of an anaerobic microorganism included in the digestive fluid is crushed.

An example methane fermentation method is configured such that the colony of the anaerobic microorganism included in the digestive fluid is crushed by mixing action of an inline mixer.

An example methane fermentation method is configured such that the colony of the anaerobic microorganism included in the digestive fluid is crushed by homogenizing action of a homogenization pump.

An example methane fermentation method is configured such that in the pulverization step, the organic substance is finely pulverized while being cooled according to the anaerobic microorganism such that the finely pulverized organic substance has a methane fermentation temperature at which the anaerobic microorganism easily acts in the methane fermentation step, and in the methane fermentation step, the organic substance having the methane fermentation temperature is supplied to the methane fermentation chamber.

An example methane fermentation method is configured such that the digestive fluid from the methane fermentation step or the concentrated liquid from the separation step is heated by heat exchange action of a heat exchanger.

An example methane fermentation system which decomposes an organic substance with an anaerobic microorganism to cause methane fermentation so as to generate methane gas includes: a wet bead mill which finely pulverizes the organic substance; a methane fermentation chamber in which the organic substance finely pulverized in the wet bead mill is decomposed with the anaerobic microorganism to cause the methane fermentation so as to generate the methane gas; a UF membrane separator which concentrates and separates a digestive fluid after the methane fermentation in the methane fermentation chamber into a concentrated liquid and a permeation liquid; and return means which returns the concentrated liquid to the methane fermentation chamber, where contents of the methane fermentation chamber are agitated by the return of the concentrated liquid with the return means.

An example methane fermentation system is configured such that the wet bead mill finely pulverizes the organic substance such that a particle diameter at 50% in a cumulative distribution with respect to a volume is equal to or less than 20 μm.

An example methane fermentation system is configured so as to include an RO membrane separator which separates the permeation liquid.

An example methane fermentation system is configured so as to include crushing means which crushes a colony of the anaerobic microorganism included in the digestive fluid after the methane fermentation in the methane fermentation chamber.

An example methane fermentation system is configured such that the crushing means is an inline mixer.

An example methane fermentation system is configured such that the crushing means is a homogenization pump.

An example methane fermentation system is configured so as to include cooling means which cools the organic substance according to the anaerobic microorganism such that the organic substance finely pulverized in the wet bead mill has a methane fermentation temperature at which the anaerobic microorganism easily acts in the methane fermentation chamber.

An example methane fermentation system is configured so as to include a heat exchanger which heats, by heat exchange action, the digestive fluid from the methane fermentation chamber or the concentrated liquid from the UF membrane separator.

According to the present invention, since the organic substance is finely pulverized in the wet bead mill, the decomposition caused by the anaerobic microorganism easily proceeds, and thus the methane gas can be efficiently generated.

Moreover, since the organic substance finely pulverized in the wet bead mill is subjected to the methane fermentation, the pores of the UF membrane are unlikely to be blocked by the digestive fluid, and the digestive fluid is easily concentrated.

Furthermore, since the contents of the methane fermentation chamber are agitated with the water flow produced by the return of the concentrated liquid, the anaerobic microorganism uniformly acts on the finely pulverized organic substance, and thus the decomposition easily proceeds.

DETAILED DESCRIPTION

The configuration of a first embodiment according to the present invention will be described in detail below with reference to FIG. 1.

Figure 1:
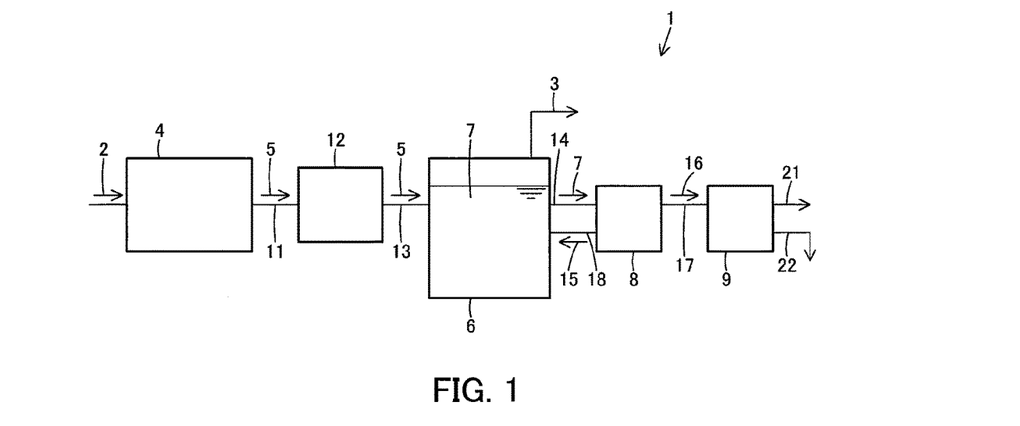
FIG. 1 is an illustrative diagram showing the configuration of a methane fermentation system according to a first embodiment of the present invention.

In FIG. 1, reference sign 1 represents a methane fermentation system, and the methane fermentation system 1 decomposes an organic waste 2 containing organic substances such as food residues, livestock manure and woody raw materials with a methane bacterium which is an anaerobic microorganism and thereby causes methane fermentation so as to generate methane gas 3.

The methane fermentation system 1 includes: a wet bead mill 4 in which the organic waste 2 is finely pulverized; and a methane fermentation chamber 6 which is filled with the methane bacterium, in which the pulverized organic substance 5 that is the organic substances finely pulverized in the wet bead mill 4 are decomposed with the methane bacterium and in which thus methane fermentation is caused to generate the methane gas 3. A UF membrane separator 8 and an RO membrane separator 9 in which a digestive fluid 7 after the methane fermentation is concentrated and separated are connected to the methane fermentation chamber 6.

The wet bead mill 4 is conventionally used when for example, a metal such as a rare metal or a paint is finely pulverized, and a raw material in a slurry state in which an item to be pulverized is mixed with a liquid is supplied per predetermined amount and beads which are put thereinto are used to perform the fine pulverization.

In the methane fermentation system 1, the organic waste 2 in a slurry state mixed with the liquid is supplied to the wet bead mill 4 per predetermined amount, and the organic waste 2 is finely pulverized into the pulverized organic substance 5. In addition, depending on the type and the state of the organic waste 2, preprocessing crushing means may be separately provided in the preceding stage such that the organic waste 2 is easily finely pulverized in the wet bead mill 4. In other words, a configuration may be adopted in which the organic waste 2 is previously crushed with the preprocessing crushing means and is mixed with the liquid into a slurry state, and in which the organic waste 2 in a slurry state is finely pulverized in the wet bead mill 4.

An organic substance storage chamber 12 is connected through a piping member 11 to the wet bead mill 4, and the pulverized organic substance 5 finely pulverized in the wet bead mill 4 is supplied through the piping member 11 to the organic substance storage chamber 12.

The organic substance storage chamber 12 is connected through a piping member 13 to the methane fermentation chamber 6, and the pulverized organic substance 5 stored in the organic substance storage chamber 12 is supplied to the methane fermentation chamber 6 per predetermined amount.

The methane fermentation chamber 6 is a sealed reaction chamber, and its interior is filled with the unillustrated methane bacterium and is kept under anaerobic conditions. Within the methane fermentation chamber 6, an agitator for performing the mixing is installed such that the methane bacterium uniformly acts on the pulverized organic substance 5.

Then, within the methane fermentation chamber 6, the pulverized organic substance 5 is decomposed with the methane bacterium to cause methane fermentation, and as the methane fermentation proceeds, the methane gas 3 and the digestive fluid 7 in which fertilizer components such as nitrogen and phosphorus are left by the decomposition of the methane are generated.

Specifically, it is highly likely that within the methane fermentation chamber 6, the methane gas generated by the methane fermentation remains in the cavity portion of the uppermost portion, and that the digestive fluid 7 is stored in a portion below it.

As the methane fermentation proceeds, a higher concentration of the methane bacterium is generated toward a lower layer of the digestive fluid 7, and since the methane bacterium is adhered to the pulverized organic substance 5, a TS (evaporation residues) concentration is increased. On the other hand, in an upper layer of the digestive fluid 7, as the methane fermentation proceeds, the concentration of the organic substances is lowered, and the TS concentration is lowered, with the result that for example, the TS concentration becomes about 2 to 5%.

In other words, within the methane fermentation chamber 6, as the methane fermentation proceeds, the methane gas 3 remains in the cavity portion of the uppermost portion, and within the digestive fluid 7 in which the fertilizer components are left, the upper layer whose TS concentration is low and the lower layer whose TS concentration is high are present. In addition, even in the upper layer of the digestive fluid whose TS concentration is low, the TS such as the pulverized organic substance 5 which is not decomposed with the methane bacterium and which is not digested is contained.

The UF membrane separator 8 is connected through a piping member 14 to the methane fermentation chamber 6, and the upper layer of the digestive fluid 7 within the methane fermentation chamber 6 is supplied to the UF membrane separator 8.

In the UF membrane separator 8, a UF membrane (ultrafiltration membrane) which includes pores having, for example, a diameter of about 0.03 µm is used, and thus the digestive fluid 7 is separated into a concentrated liquid 15 that contains the TS such as the pulverized organic substance 5 which does not pass the pores and which is formed in the shape of fine particles and a permeation liquid 16 which passes the pores.

The RO membrane separator 9 is connected through a piping member 17 to the UF membrane separator 8, and the permeation liquid 16 is supplied from the UF membrane separator 8 to the RO membrane separator 9.

Also, the methane fermentation chamber 6 is connected to the UF membrane separator 8 through a piping member 18 which is a return path and which serves as return means, and the concentrated liquid 15 is returned from the UF membrane separator 8 to the methane fermentation chamber 6.

Then, the concentrated liquid 15 is returned from the UF membrane separator 8 to the methane fermentation chamber 6, and thus a water flow is produced within the methane fermentation chamber 6, with the result that the contents of the methane fermentation chamber 6 are agitated by this water flow.

In addition, although it is likely that the digestive fluid 7 within the methane fermentation chamber 6 is not clearly separated into the upper layer whose TS concentration is low and the lower layer whose TS concentration is high, the piping member 14 and the piping member 18 serving as circulation lines between the methane fermentation chamber 6 and the UF membrane separator 8 are constantly kept in an anaerobic state, and thus the UF membrane is not blocked even in a state where the upper layer and the lower layer of the digestive fluid 7 are partially mixed, with the result that the action of enhancing or maintaining the overall TS concentration within the methane fermentation chamber 6 caused by returning the concentrated liquid 15 is prevented from being lowered.

Since the concentrated liquid 15 is returned to the methane fermentation chamber 6, the methane fermentation in the methane fermentation chamber 6, the concentration and separation of the digestive fluid 7 in the UF membrane separator 8, the return of the concentrated liquid 15 from the UF membrane separator 8 to the methane fermentation chamber 6 and the agitation of the contents of the methane fermentation chamber 6 caused by the return are substantially repeated.

The RO membrane separator 9 separates, with an RO membrane (reverse osmosis membrane), the permeation liquid 16 on an ion level. In other words, even the permeation liquid 16 which is separated from the concentrated liquid 15 in the UF membrane separator 8 contains ionized components and thus cannot be drained without being processed with consideration given to drainage standards and the like. Hence, in the RO membrane separator 9, the permeation liquid 16 is separated into concentrated water 21 containing the fertilizer components and permeation water 22 which can be drained.

Then, the discharged amount of concentrated water 21 obtained in the RO membrane separator 9 can be reduced to 30% or less of the input amount of organic waste 2 and can be reused as a liquid fertilizer whose concentration is higher than normal.

Also, the permeation water 22 obtained in the RO membrane separator 9 can be processed, as necessary, such as by being reused in an application such as for diluting the organic substances or the like or by being drained.

A methane fermentation method in the methane fermentation system 1 described above will then be described.

When the organic waste 2 serving as organic substance is decomposed with the methane bacterium and is subjected to methane fermentation so as to generate the methane gas 3, the organic waste 2 is first finely pulverized in the wet bead mill 4.

When the organic waste 2 is finely pulverized, the organic waste 2 and water are mixed with each other so as to be brought into a slurry state. In addition, when the preprocessing crushing means is installed in the preceding stage, the organic waste 2 may be brought into a slurry state by being crushed with the preprocessing crushing means and also being mixed with water.

Here, in order for the organic waste 2 to be pulverized in the wet bead mill 4, the moisture content of the slurry is very important. Specifically, for example, when a metal such as a rare metal is conventionally pulverized in the wet bead mill 4, the moisture content is adjusted such that the slurry contains a solid content of 15 to 30%. However, since the specific gravity of the organic waste 2 is less than 2, is less than that of the metal and is less than that of water, is slightly less than that of water or is equal to that of water, the proceeding state of the pulverization in the wet bead mill 4 differs from the metal. In other words, since the organic waste 2 contains an amino acid, lignin, a protein and the like, as the pulverization proceeds, the viscosity thereof is increased. When the viscosity is excessively increased, the circulation of the organic waste 2 within the wet bead mill 4 is inhibited, and thus it is difficult for the pulverization to proceed, with the result that it is impossible to pulverize the organic waste 2 into a predetermined size.

Hence, preferably, when the organic waste 2 is pulverized in the wet bead mill 4, the moisture is adjusted such that the solid content in the slurry is equal to or less than 10% (TS).

The organic waste 2 in a slurry state whose moisture is adjusted as described above is supplied per predetermined amount to the wet bead mill 4 and is finely pulverized.

Since the solid content in the organic waste 2 in a slurry state is equal to or less than 10%, in the early stage of the pulverization, the viscosity of the organic waste 2 in a slurry state in the process of the pulverization is not achieved, and when in such a state, the bead mill 4 is rotated at a high speed, the organic waste 2 cannot be appropriately pulverized, and the size of a center vortex may be increased such that an overflow occurs.

Hence, for 30 minutes after the start of the pulverization, the pulverization is performed by rotating the bead mill at a medium speed, and after 30 minutes have elapsed since the start of the pulverization and a certain degree of viscosity is achieved, the pulverization is performed by rotating the bead mill at the maximum speed for up to two hours.

As described above, the bead mill is rotated at a medium speed in the early stage of the pulverization, then the bead mill is rotated at a high speed and thus it is possible to appropriately and finely pulverize the organic waste 2 such that for example, the particle diameter (median diameter) at 50% in a cumulative distribution (accumulated distribution) with respect to the volume is equal to or less than 20 µm. In addition, it is more preferable to pulverize the organic waste 2 such that the median diameter of the organic waste 2 is equal to or more than 0.8 µm and equal to or less than 10 µm.

The pulverized organic substance 5 which is finely pulverized is temporarily stored in the organic substance storage chamber 12, and is supplied per predetermined amount to the methane fermentation chamber 6.

Then, the pulverized organic substance 5 is decomposed with the methane bacterium within the methane fermentation chamber 6 so as to cause methane fermentation, and thus the methane gas 3 is generated and the digestive fluid 7 in which the other fertilizer components such as nitrogen and phosphorus are left by the decomposition of the methane is generated.

The methane gas 3 generated by the methane fermentation is collected as necessary and is utilized as, for example, an energy source for an engine generator.

In the digestive fluid 7 generated by the methane fermentation, the TS concentration of the upper layer is relatively low, the TS concentration of the lower layer is relatively high and the methane fermentation proceeds in the lower layer. Hence, the upper layer whose TS concentration is low is supplied to the UF membrane separator 8.

In the UF membrane separator 8, the digestive fluid 7 is separated, with the UF membrane, into the concentrated liquid 15 containing the TS and the permeation liquid 16 passing the pores of the UF membrane. In addition, since bacteria, germs and the like cannot pass the pores (for example, a diameter of about 0.03 µm) of the UF membrane, even when the methane bacterium is contained in the digestive fluid 7, the methane bacterium is separated together with the concentrated liquid 15.

Since the concentrated liquid 15 separated in the UF membrane separator 8 in this way has, as the main component, TS components containing the methane bacterium, the concentrated liquid 15 is returned to the methane fermentation chamber 6 and is utilized for reducing a decrease in the TS concentration within the methane fermentation chamber 6 whereas the permeation liquid 16 containing the fertilizer components which contain almost no TS components and which are ionized is supplied to the RO membrane separator 9.

In addition, the concentrated liquid 15 is returned to the methane fermentation chamber 6, and thus the water flow is produced within the methane fermentation chamber 6, with the result that the contents of the methane fermentation chamber 6 are agitated by this water flow.

In the RO membrane separator 9, the permeation liquid 16 is separated, with the RO membrane, into the concentrated water 21 containing the fertilizer components and the permeation water 22 which can be drained.

Then, the concentrated water 21 is reused as a liquid fertilizer, and the permeation water 22 is reused as dilution water or is drained.

The action and effects of the first embodiment discussed above will then be described.

In the methane fermentation system 1 and the methane fermentation method described above, even when the organic waste 2 contains an organic component such as a woody or fibrous component in which it is difficult for the decomposition with the methane bacterium to proceed, since the organic waste 2 is finely pulverized in the wet bead mill 4 into such a size that it is impossible to pulverize the organic waste 2 into the size with a conventional crusher or the like, the decomposition with the methane bacterium easily proceeds, with the result that it is possible to enhance a methane conversion rate, to reduce a decomposition time and to efficiently generate the methane gas.

In particular, the organic waste 2 is finely pulverized in the wet bead mill 4 such that the particle diameter at 50% in the cumulative distribution with respect to the volume is equal to or less than 20 µm, and thus the decomposition of the organic waste 2 with the methane bacterium easily proceeds, with the result that it is possible to more efficiently generate the methane gas.

Also, when the organic waste 2 is crushed with, for example, a crusher as conventionally performed, since the particle diameter of the undigested TS contained in the digestive fluid 7 is large with respect to the pore of the UF membrane, the pores are blocked when the digestive fluid 7 is separated with the membrane in the UF membrane separator 8. Specifically, when the digestive fluid 7 to be separated contains just a few percent of a substance having a diameter of 4 mm or more, the pores of the UF membrane is blocked.

However, as described above, the organic waste 2 is finely pulverized in the wet bead mill 4 such that the median diameter is equal to or less than 20 µm, and thus the pores of the UF membrane are seldom blocked by the undigested pulverized organic substance 5 contained in the digestive fluid 7.

In other words, the organic waste 2 is finely pulverized such that the median diameter is equal to or less than 20 µm, and thus when the digestive fluid 7 after the methane fermentation is concentrated in the UF membrane separator 8, the pores of the UF membrane are unlikely to be blocked by the undigested pulverized organic substance 5 left in the digestive fluid 7, with the result that it is possible to smoothly concentrate the digestive fluid 7.

When the organic waste 2 is finely pulverized in the wet bead mill 4, the moisture content of the organic waste 2 is adjusted such that the solid content is equal to or less than 10%, and thus it is possible to prevent the viscosity from being excessively increased in the process of the pulverization, with the result that it is possible to finely pulverize the organic waste 2 into a desired particle size, for example, a median diameter of 20 µm or less.

Here, for example, since when membrane separation is performed, the membrane separation is normally started in a state where a moisture content is previously reduced, the membrane separation is stepwise performed so as not to block the membrane. Then, when the moisture content is normally reduced so as to increase the solid of the organic waste 2 in a slurry state, and the concentration is performed in the UF membrane separator 8 after the pulverization and the methane fermentation, the pores of the UF membrane are highly likely to be blocked. Hence, the moisture content of the organic waste 2 in a slurry state is adjusted before the methane fermentation (before the fine pulverization) such that the solid content is equal to or less than 10%, and thus it is possible to acquire the fluidity of the digestive fluid 7 and to prevent the UF membrane from being blocked by the fact that when the digestive fluid 7 is concentrated, the concentration of the solid in the digestive fluid 7 is increased and thus the fluidity is lowered, with the result that the digestive fluid 7 is easily concentrated.

Hence, the moisture content of the organic waste 2 is adjusted, and thus it is possible to appropriately finely pulverize the organic waste 2, to make the methane fermentation easily proceed and to easily concentrate the digestive fluid 7 after the methane fermentation, with the result that a series of steps from the methane fermentation to the concentration and separation can be made to proceed efficiently.

The digestive fluid 7 after the methane fermentation is concentrated and separated with the UF membrane, and thus the TS such as the pulverized organic substance 5 contained in the digestive fluid 7 can be concentrated and separated from the digestive fluid 7, and the concentrated liquid 15 containing the TS is returned to the methane fermentation chamber 6, and thus it is possible to perform the methane fermentation without waste and efficiently.

Also, the concentrated liquid 15 is returned from the UF membrane separator 8 to the methane fermentation chamber 6, and thus the water flow is produced within the methane fermentation chamber 6 so as to have the action of agitating the contents of the methane fermentation chamber 6, with the result that the power of the agitator installed within the methane fermentation chamber 6 can be reduced.

Furthermore, the digestive fluid 7 contains a large number of ionized components, and among them, ammonia is a component which inhibits the methane fermentation when the concentration thereof is increased within the methane fermentation chamber 6 but the digestive fluid 7 is separated with the UF membrane and thus the ionized components can be separated from the digestive fluid 7 and the concentrated liquid 15, with the result that it is possible to reduce the risk of inhibiting the methane fermentation.

The permeation liquid 16 after the concentration and separation with the UF membrane is separated with the RO membrane, and thus the permeation liquid 16 can be purified enough to be drained and can be processed easily and appropriately. In other words, since the ionized components contained in the permeation liquid 16 can be separated with the RO membrane as the concentrated water 21, the concentrated water 21 containing the fertilizer components such as ammonia nitrogen, phosphorus, potassium and the like which are ionized can be effectively utilized as a concentrated liquid fertilizer or the like, and the permeation water 22 can be reused or be drained without being processed.

Although it can be considered that the amount of low-concentration liquid fertilizer obtained by the methane fermentation is significant, and that thus it is disadvantageously difficult to utilize it with consideration given to a transportation method, an operation method and the like, the concentration and separation are performed with the UF membrane and the RO membrane, and thus it is possible not only to obtain a high-concentration liquid fertilizer as the concentrated water 21 but also to reduce the volume to, for example, a fifteenth to a tenth as compared with a conventional concentrating/separating method, with the result that it is possible to cope with the problems in the transportation and the operation.

In addition, although in the first embodiment described above, as the raw material, the organic waste 2 is used, there is no limitation to such a configuration, and as long as an organic substance is contained, a raw material which is not a waste can be applied.

Also, although the digestive fluid 7 after the methane fermentation is concentrated and separated with the UF membrane, and the concentrated and separated permeation liquid 16 is concentrated and separated with the RO membrane, there is no limitation to such a configuration, and the permeation liquid 16 may be processed such as by being concentrated and separated in another method.

A second embodiment will then be described with reference to FIG. 2. The same configurations and action as in the first embodiment are identified with the same reference signs, and the description thereof will be omitted.

Figure 2:
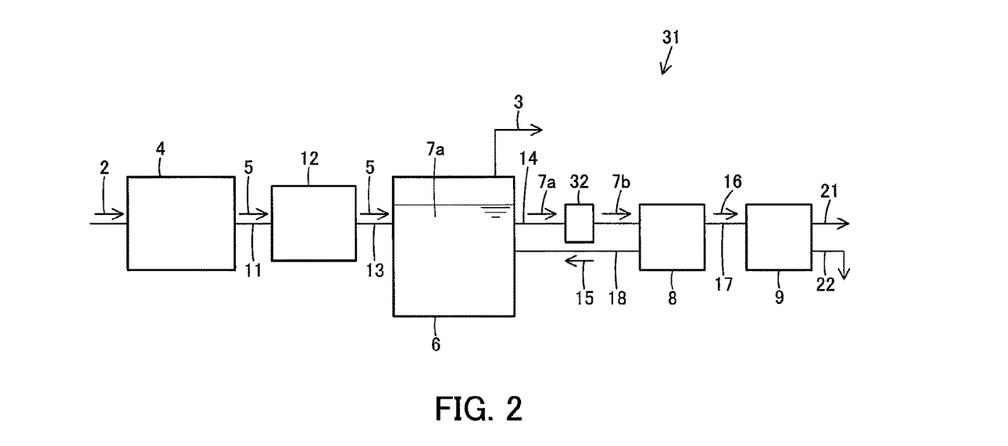
FIG. 2 is an illustrative diagram showing the configuration of a methane fermentation system according to a second embodiment of the present invention.

As shown in FIG. 2, as crushing means for crushing the colony of methane bacteria contained in a digestive fluid 7a after methane fermentation, an inline mixer 32 is connected to a methane fermentation chamber 6 in a methane fermentation system 31, and a UF membrane separator 8 and an RO membrane separator 9 in which the digestive fluid 7b after the colony is crushed is concentrated and separated are connected to the downstream side of the inline mixer 32.

Here, in the methane fermentation chamber 6, in order for the methane fermentation to proceed, an organic substance raw material, a fermentation temperature, pH, a small amount of inorganic salt metal and a fermentation inhibiting factor are controlled, and thus the balance between the growth and death of the methane bacteria is held, with the result that the growth and death are managed to be in an equilibrium state.

In the course of the growth of the methane bacteria, the methane bacteria form a colony (bacterial colony) which is an aggregation of the grown bacteria.

Also, since the methane bacterium itself is significantly lightweight, the colony which is an aggregation of the methane bacteria is not precipitated within the methane fermentation chamber 6, and in the digestive fluid 7a, the colony is floated in the shape of, for example, a biofilm (biological film) or forms an upper layer surface of the digestive fluid 7a.

The colony of the methane bacteria described above may block the UF membrane of the UF membrane separator 8. In other words, when the digestive fluid 7a containing the colony of the methane bacteria is concentrated and separated in the UF membrane separator 8, the pores of the UF membrane may be clogged by the colony and thus the UF membrane may be blocked.

Hence, in a piping member 14 between the methane fermentation chamber 6 and the UF membrane separator 8, the inline mixer 32 is provided, and the digestive fluid 7a passes the inline mixer 32, with the result that the colony in the digestive fluid 7a is crushed and that the methane bacteria are broken apart. In other words, with a shear force based on the mixing action of the inline mixer 32 when the digestive fluid 7a passes the inline mixer 32, the colony in the digestive fluid 7a is crushed.

The digestive fluid 7a passes the inline mixer 32, thus the colony is crushed and a digestive fluid 7b whose TS concentration is low is supplied to the UF membrane separator 8.

Also, a concentrated liquid 15 after the concentration and separation with the UF membrane separator 8 is returned to the methane fermentation chamber 6, and thus the methane fermentation in the methane fermentation chamber 6, the crushing of the colony in the digestive fluid 7a with the inline mixer 32, the concentration and separation of the digestive fluid 7b in the UF membrane separator 8, the return of the concentrated liquid 15 from the UF membrane separator 8 to the methane fermentation chamber 6 and the agitation of the contents of the methane fermentation chamber 6 are substantially repeated.

In the methane fermentation system 31 described above, the colony included within the digestive fluid 7a from the methane fermentation chamber 6 is crushed with the inline mixer 32, and thus the methane bacteria are broken apart, with the result that it is possible to prevent the pores of the UF membrane from being blocked (clogged) by the colony. Hence, it is possible to appropriately concentrate and separate the digestive fluid 7b with the UF membrane separator 8 and to make the methane fermentation proceed efficiently by returning the concentrated liquid 15 to the methane fermentation chamber 6.

Also, after the colony of the methane bacteria in the digestive fluid 7a from the methane fermentation chamber 6 is crushed, the concentrated liquid 15 concentrated in the UF membrane separator 8 is returned to the methane fermentation chamber 6 and is circulated, and thus as compared with a case where within the methane fermentation chamber 6, the methane bacteria continue to be present as the colony, it is possible to increase the surface area of the methane bacteria. Hence, the digesting action and the growing action of the pulverized organic substance 5 of the methane bacteria in the methane fermentation chamber 6 can be facilitated, with the result that it is possible to enhance the efficiency of the methane fermentation.

Since the inline mixer 32 can be provided in the piping member 14 between the methane fermentation chamber 6 and the UF membrane separator 8, the inline mixer 32 can be easily installed, and a mixing tank or the like is not needed, with the result that the facilities are prevented from being enlarged.

Also, since the organic waste 2 is finely pulverized in the wet bead mill 4 such that the median diameter is equal to or less than 20 μm, and the colony included in the digestive fluid 7a is crushed with the inline mixer 32, the UF membrane separator 8 is unlikely to be blocked by the organic waste 2 and the colony, with the result that the small pulverized organic substance 5 and the broken methane bacteria easily act. In other words, by synergy of the configuration in which the organic waste 2 is finely pulverized and the configuration in which the colony included in the digestive fluid 7a is crushed, it is possible to make the methane fermentation in the methane fermentation chamber 6 and the concentration and separation in the UF membrane separator 8 smoothly proceed. Hence, it is possible to make a series of steps from the methane fermentation to the concentration and separation efficiently proceed, and it is also possible to enhance the efficiency of the methane fermentation by returning and circulating the concentrated liquid 15 from the UF membrane separator 8 to the methane fermentation chamber 6.

In addition, although in the second embodiment described above, the inline mixer 32 is used as the crushing means, there is no limitation to such a configuration, and as long as the crushing means can crush the colony in the digestive fluid 7a, any configuration may be adopted.

Specifically, for example, as the crushing means, a homogenization pump (homogenizer) may be used.

In the configuration in which the homogenization pump is used as the crushing means, by the homogenizing action of the homogenization pump, the synergy of shear, crash, cavitation and the like is instantaneously produced, and thus the colony in the digestive fluid 7a is crushed.

Then, the homogenization pump can be utilized not only as the crushing means for crushing the colony but also as a drive source for supplying the digestive fluids 7a and 7b from the methane fermentation chamber 6 to the UF membrane separator 8, and thus it is possible to simplify the facilities.

A third embodiment will then be described with reference to FIG. 3. The same configurations and action as in the first embodiment are identified with the same reference signs, and the description thereof will be omitted.

Figure 3:
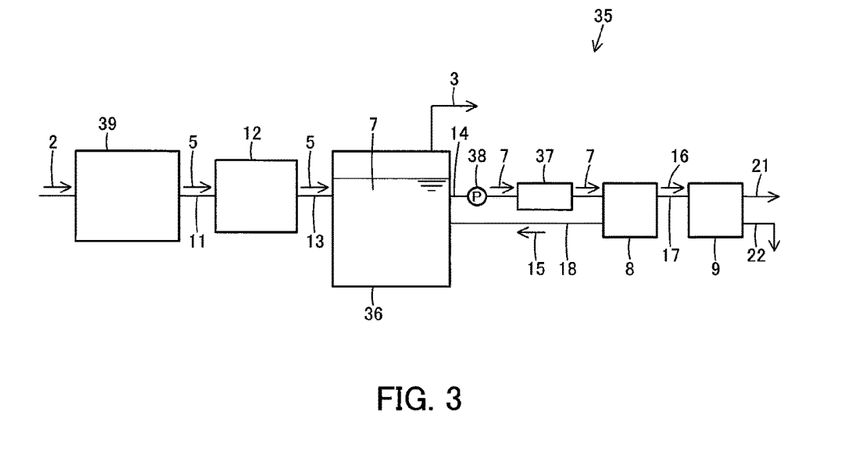
FIG. 3 is an illustrative diagram showing the configuration of a methane fermentation system according to a third embodiment of the present invention.

As shown in FIG. 3, a UF membrane separator 8 and an RO membrane separator 9 are connected to a methane fermentation chamber 36 in a methane fermentation system 35 through a heat exchanger 37 for heating a digestive fluid 7.

Here, a methane bacterium differs depending on the type thereof in a temperature suitable for the synthesis of methane (methane fermentation temperature). For example, in the case of a so-called medium-temperature fermentation methane bacterium, a temperature of about 38° C. is suitable for the synthesis of methane whereas in the case of a so-called high-temperature fermentation methane bacterium, a temperature of about 55° C. is suitable for the synthesis of methane.

In other words, in order to make the methane fermentation appropriately proceed in the methane fermentation chamber 36, it is important to keep the interior of the methane fermentation chamber 36 at the methane fermentation temperature at which the methane bacterium easily acts.

Hence, by the heat exchange action of the heat exchanger 37 which is provided between the methane fermentation chamber 36 and the UF membrane separator 8 through a pump 38 serving as a power source for circulation, a digestive fluid 7 is heated to a predetermined temperature.

Also, since the heat exchanger 37 is provided in a circulation path from the methane fermentation chamber 36 through the UF membrane separator 8, the supply of the digestive fluid 7 from the methane fermentation chamber 36 to the heat exchanger 37, the supply of the digestive fluid 7 from the heat exchanger 37 to the UF membrane separator 8 and the return of a concentrated liquid 15 from the UF membrane separator 8 to the methane fermentation chamber 36 are performed by drive of the one pump 38.

Then, the digestive fluid 7 from the methane fermentation chamber 36 is heated by the heat exchanger 37 and is supplied to the UF membrane separator 8, and the concentrated liquid 15 from the UF membrane separator 8 is returned to the methane fermentation chamber 36 and is circulated.

Also, the digestive fluid 7 is heated and circulated as described above, and thus a substantially total amount of contents of the methane fermentation chamber 36 is heated, with the result that the interior of the methane fermentation chamber 36 is heated to the methane fermentation temperature. In other words, by the return of the concentrated liquid 15 after the concentration and separation in the UF membrane separator 8, the heat exchanger 37 is controlled to heat the digestive fluid 7 such that the interior of the methane fermentation chamber 36 becomes the methane fermentation temperature.

Also, in order for the temperature of the interior of the methane fermentation chamber 36 not to be easily changed by a pulverized organic substance 5 supplied, in a wet bead mill 39, the pulverized organic substance 5 is finely pulverized while being cooled according to the methane bacterium within the methane fermentation chamber 36 such that the pulverized organic substance 5 finely pulverized has the methane fermentation temperature at which the methane bacterium easily acts within the methane fermentation chamber 36.

Specifically, the temperature is managed by cooling the tank of the wet bead mill 39 to which the organic waste 2 is supplied such that the temperature of the finely pulverized substance within the tank becomes the methane fermentation temperature. For example, in the case of the medium-temperature fermentation methane bacterium, the cooling of the tank is controlled such that the temperature of the finely pulverized substance within the tank of the wet bead mill 39 becomes about 38° C. whereas in the case of the high-temperature fermentation methane bacterium, the cooling of the tank is controlled such that the temperature of the finely pulverized substance within the tank of the wet bead mill 39 becomes about 55° C.

An organic substance storage chamber 12 is connected to the wet bead mill 39 through a piping member 11, and the pulverized organic substance 5 which is finely pulverized in the wet bead mill 39 is supplied through the piping member 11 to the organic substance storage chamber 12.

The organic substance storage chamber 12 has a heat retention structure capable of retaining the temperature of the contents, and the pulverized organic substance 5 which is finely pulverized while being cooled to the methane fermentation temperature in the wet bead mill 39 is stored in the organic substance storage chamber 12 in a state where the temperature of the pulverized organic substance 5 is retained.

The organic substance storage chamber 12 is connected through a piping member 13 to the methane fermentation chamber 36, and the pulverized organic substance 5 stored in the organic substance storage chamber 12 in the temperature-retained state is supplied to the methane fermentation chamber 36 per predetermined amount.

Then, in the methane fermentation system 35 described above, since the organic waste 2 is finely pulverized while being cooled to the methane fermentation temperature in the wet bead mill 39, a change in the temperature within the methane fermentation chamber 36 caused by the supply of the pulverized organic substance 5 can be reduced by the utilization of thermal energy generated by the fine pulverization of the organic waste 2. Hence, the thermal energy generated by the fine pulverization is utilized for managing the temperature within the methane fermentation chamber 36, and thus the energy for heating the interior of the methane fermentation chamber 36 to the methane fermentation temperature is reduced, with the result that it is possible to make the methane fermentation proceed efficiently.

Also, since the wet bead mill 39 is cooled according to the methane bacterium of the methane fermentation chamber 36 such that the finely pulverized organic waste 2 has the methane fermentation temperature, the methane bacterium within the methane fermentation chamber 36 is prevented from being inactivated by the heat of the pulverized organic substance 5 supplied to the methane fermentation chamber 36, and thus it is possible to make the methane fermentation with the methane bacterium appropriately proceed.

The digestive fluid 7 after the methane fermentation in the methane fermentation chamber 36 is heated to a predetermined temperature by the heat exchange action of the heat exchanger 37 provided between the methane fermentation chamber 36 and the UF membrane separator 8 in the circulation path and is then supplied to the UF membrane separator 8, with the result that the one pump 38 can serve both as a power source for supplying the digestive fluid 7 to the heat exchanger 37 and thereby heating it and as a power source for supplying the digestive fluid 7 to the UF membrane separator 8. In other words, the heat exchanger 37 for heating the interior of the methane fermentation chamber 36 is provided in the circulation path, and thus the power source for the heating does not need to be provided separately of the power source for the circulation (the concentration and separation and the return), with the result that the power cost is reduced and that it is possible to make the methane fermentation proceed efficiently.

In addition, for example, when a configuration is adopted in which means for heating a heat pipe and the like is incorporated in the methane fermentation chamber 36 itself in order to heat the interior of the methane fermentation chamber 36 to the methane fermentation temperature, it is likely that scale is produced on the outer surface and the inner surface of the heat pipe. It is very difficult to perform a maintenance operation of, for example, removing such scale and replacing the heat pipe in the configuration in which the heat pipe and the like are provided in the methane fermentation chamber 36 itself, and thus it may be impossible to appropriately manage the temperature within the methane fermentation chamber 36 by stopping the heating of the interior of the methane fermentation chamber 36, with the result that it may be impossible to make the methane fermentation efficiently proceed.

Hence, the heat exchanger 37 which is the means for heating the interior of the methane fermentation chamber 36 to the methane fermentation temperature is provided outside (between the methane fermentation chamber 36 and the UF membrane separator 8) the methane fermentation chamber 36, and thus it is possible to avoid the risk on the maintenance, the replacement and the like, and it is also possible to efficiently perform the operation by the utilization of the power source for the circulation as described above.

In addition, although the configuration in which as in the third embodiment described above, the heat exchanger 37 for heating the interior of the methane fermentation chamber 36 to the methane fermentation temperature is provided in the circulation path is preferable because the one power source can serve both as the power source for the heating and the power source for the circulation, there is no limitation to such a configuration, and the configuration and the installation position of the heating means for heating the interior of the methane fermentation chamber 36 to the methane fermentation temperature can be determined as necessary.

Also, in the case of the configuration in which the heat exchanger 37 is provided in the circulation path, there is no limitation to the configuration in which the digestive fluid 7 from the methane fermentation chamber 36 is heated between the methane fermentation step and the separation step, and a configuration may be adopted in which the concentrated liquid 15 is heated between the separation step and the return step.

In addition, a configuration obtained by combining the second embodiment and the third embodiment described above may be adopted. In other words, for example, between the pump 38 and the heat exchanger 37 shown in FIG. 3, the inline mixer 32 which is the crushing means may be provided or instead of the pump 38 shown in FIG. 3, the homogenization pump which is the crushing means may be provided.

EXAMPLES

Examples and comparative example will be described below.

The efficiency of methane fermentation caused by a difference in the particle size of an organic substance was first checked.

Figure 4:
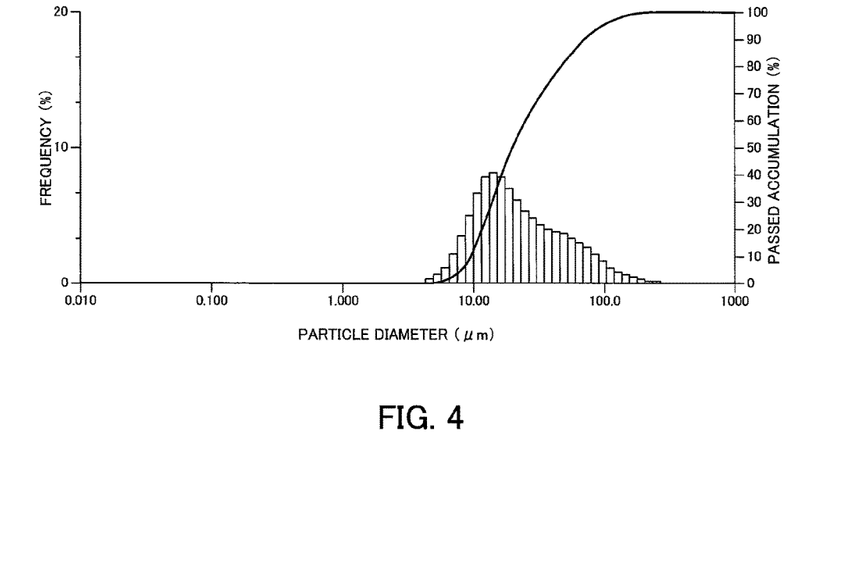
FIG. 4 is a graph showing a particle size distribution in Example 1.

An organic substance whose moisture content was adjusted so as to have a slurry state where a solid was about 7% was pulverized in a wet bead mill for one hour, and the pulverized sample was used for Example 1. The particle size distribution of the sample in Example 1 is shown in FIG. 4.

In Example 1, the median diameter which was a particle diameter at 50% in a cumulative distribution with respect to the volume was 19.7 μm, and the arithmetic standard deviation was 31.1 μm.

Figure 5:
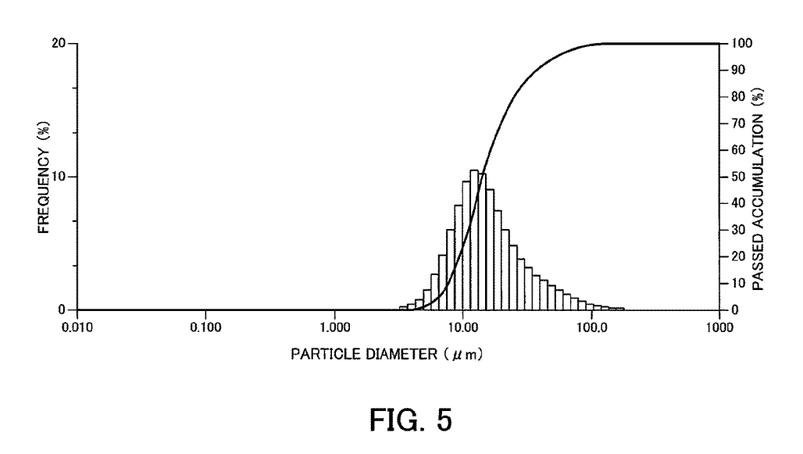
FIG. 5 is a graph showing a particle size distribution in Example 2.

An organic substance whose moisture content was adjusted as in Example 1 was pulverized in the wet bead mill for one and a half hours, and the pulverized sample was used for Example 2. The particle size distribution of the sample in Example 2 is shown in FIG. 5.

In Example 2, the median diameter was 14.4 μm, and the arithmetic standard deviation was 17.4 μm.

Figure 6:
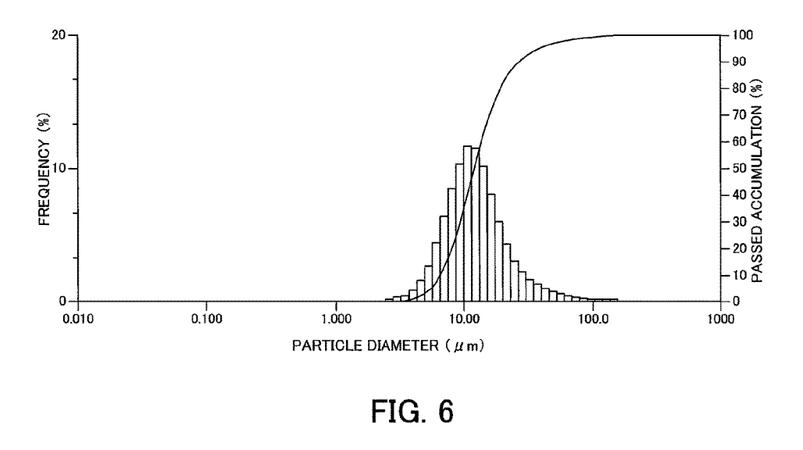
FIG. 6 is a graph showing a particle size distribution in Example 3.

An organic substance whose moisture content was adjusted as in Examples 1 and 2 was pulverized in the wet bead mill for two hours, and the pulverized sample was used for Example 3. The particle size distribution of the sample in Example 3 is shown in FIG. 6.

In Example 3, the median diameter was 11.9 μm, and the arithmetic standard deviation was 12.6 μm.

Also, an organic substance was crushed, as in a conventional manner, with a crushing mixer so as to have a particle diameter of 1 to 5 mm, and the crushed sample was used for Comparative Example.

In these Examples and Comparative Example, the same methane bacterium was used, methane fermentation was performed under the same conditions and the amount of methane generated and a methane conversion rate were measured.

Figure 7:
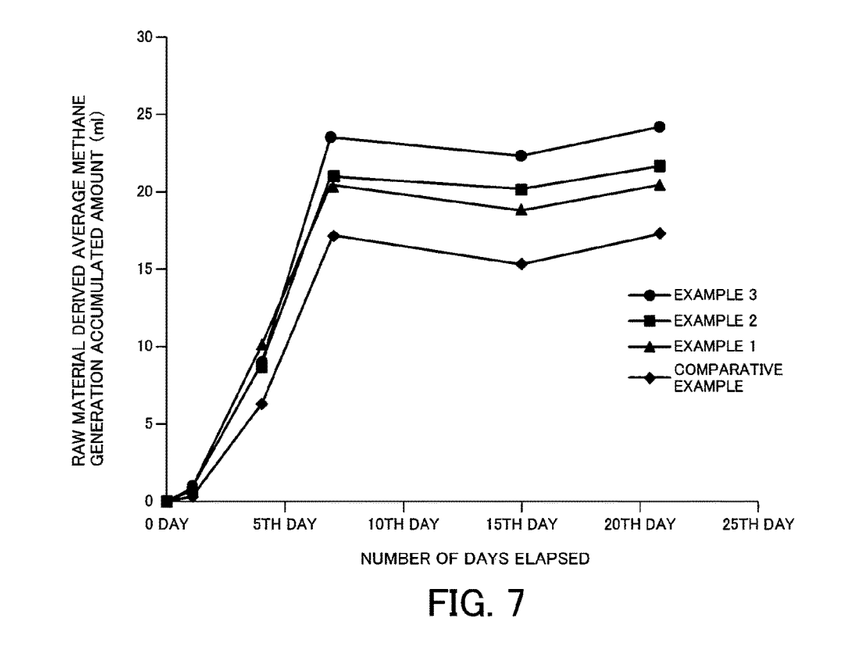
FIG. 7 is a graph showing the amount of methane generated in Examples and Comparative Example.
Figure 8:
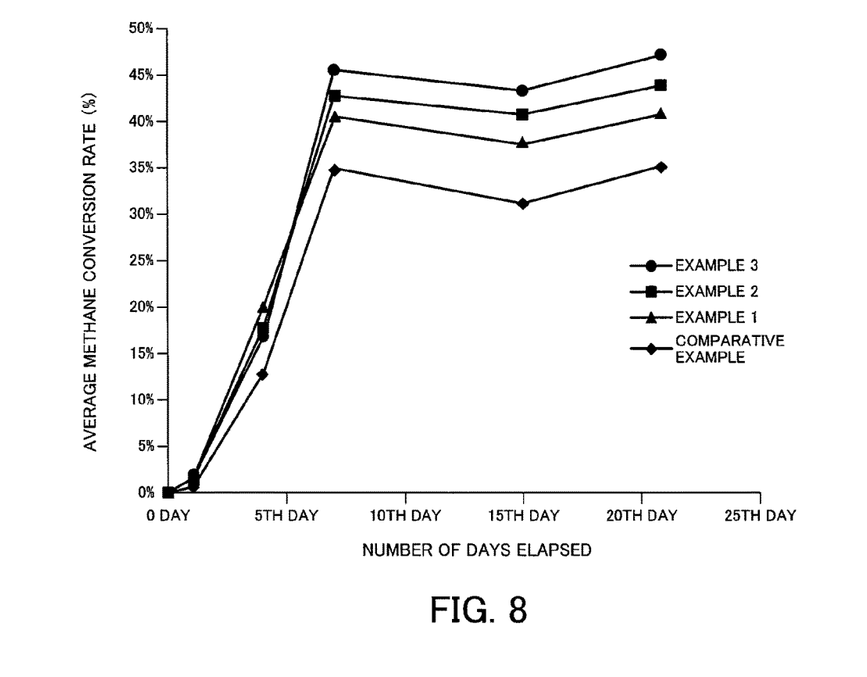
FIG. 8 is a graph showing a methane conversion rate in the Examples and the Comparative Example.

In the Examples and Comparative Example, the averages of the amounts of methane generated in three specimens were shown in FIG. 7, and the averages of the methane conversion rates in the three specimens were shown in FIG. 8.

As shown in FIGS. 7 and 8, in all of examples 1 to 3 where the organic substance was finely pulverized in the wet bead mill, as compared with the Comparative Example where the organic substance was processed with the crushing mixer, the amount of methane generated and the methane conversion rate were satisfactory, differences were produced immediately after the start of the methane fermentation and the proceeding speed of the methane fermentation clearly differed.

size of the organic substances after being pulverized to be checked, the amounts of individual samples were aligned with COD values, and a BMP (Biochemical Methane Production) test was performed according to ISO14853.

The samples which were obtained by finely pulverizing the organic substances in the wet bead mill to have a particle diameter of 2 to 10 μm were assumed to be nano-processed products (Examples), the samples which were likewise obtained by finely pulverizing the organic substances to have a particle diameter of 100 to 500 μm were assumed to be micro-processed products (Examples) and the sample which was obtained by processing, with the crushing mixer, the organic substance to have a particle diameter of 1 to 5 mm was assumed to be a mixer-processed product (Comparative Example).

The micro-processed products and the nano-processed products in the Examples and the mixer-processed product in the Comparative Example were dried at 110° C. for two hours, thereafter the weights thereof were measured and the TS thereof were determined.

Also, for the micro-processed products and the nano-processed products in the Examples, 20 μl was weighed and was put into a vial for COD reaction (100-fold dilution) together with 1980 μl of water and the COD thereof was measured.

For the mixer-processed product in the Comparative Example, 2.0 mg was put into the vial for COD reaction together with 2000 μl of water, and the COD thereof was measured with a measuring device of HACH Company.

In the BMP test, the vial bottle (final volume of 50 ml) was sealed, was then subjected to nitrogen substitution and was placed within a constant temperature oven of 55° C.

Then, a biogas which was generated over time was collected, the generated amount was measured, methane gas and $CO_2$ components were measured by gas chromatography and the methane conversion rate was calculated.

Figure 9:
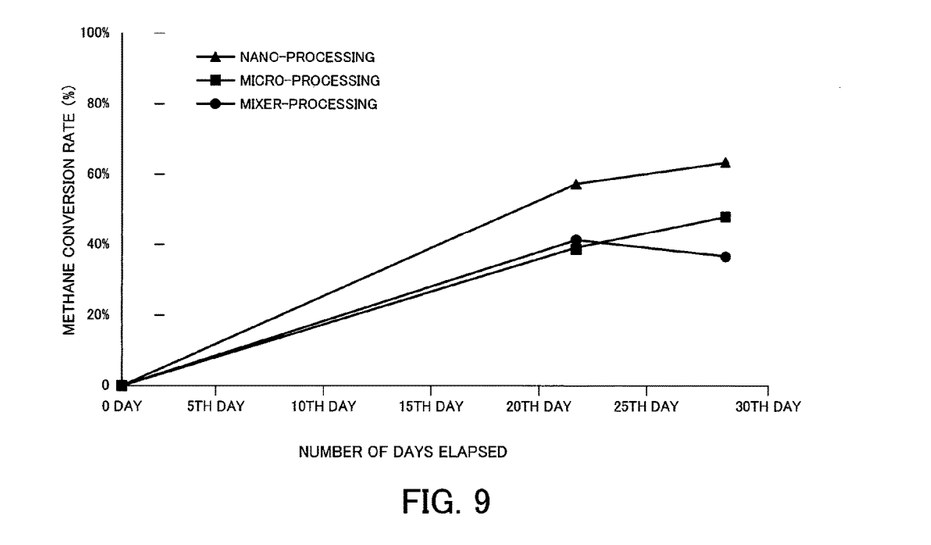
FIG. 9 is a graph showing the methane conversion rate in the Examples and the Comparative Example when sorghum is used as the organic substance.

Each of the measurements described above was performed on three specimens in each of the samples. The results of the measurements are shown in Table 1. The transition of the methane conversion rate in each of the samples is shown in FIG. 9.

TABLE 1

| Sample | Sludge | Water | Amount of sample | gCOD/TS | COD (mg/l) | TS (%) | Input amount (g) | Input amount (ml) | Input COD (g) | CH4max (ml) |
|---|---|---|---|---|---|---|---|---|---|---|
| Mixer-processed 1 | 80 g | 20 g | 0.2 g | 1.28 | — | 91.45 | 0.22 | — | 0.2572 | 98.27 |
| Mixer-processed 2 | | | | 1.28 | — | 91.45 | 0.22 | — | 0.2572 | 98.27 |
| Mixer-processed 3 | | | | 1.28 | — | 91.45 | 0.22 | — | 0.2572 | 98.27 |
| Micro-processed 1 | 80 g | 17.7 g | 2.3 ml | — | 77,700 | — | — | 3.4 | 0.2642 | 100.93 |
| Micro-processed 2 | | | | — | 77,700 | — | — | 3.4 | 0.2642 | 100.93 |
| Micro-processed 3 | | | | — | 77,700 | — | — | 3.4 | 0.2642 | 100.93 |
| Nano-processed 1 | 80 g | 15.3 g | 4.7 ml | — | 51,600 | — | — | 5.0 | 0.2580 | 98.57 |
| Nano-processed 2 | | | | — | 51,600 | — | — | 5.0 | 0.2580 | 98.57 |
| Nano-processed 3 | | | | — | 51,600 | — | — | 5.0 | 0.2580 | 98.57 |

When examples 1 to 3 are compared with each other, as the time during which the organic substance was pulverized in the wet bead mill was longer, and the particle diameter was smaller, the amount of methane generated, the methane conversion rate and the proceeding speed of the methane fermentation were more satisfactory.

Then, as the organic substance, sorghum, palm or coffee grounds were used, and in order for the efficiency of methane fermentation caused by a difference in the particle When the sorghum was used as the organic substance, as shown in Table 1, methane gas was generated in each of the nano-processing, the micro-processing and the mixer-processing.

As shown in FIG. 9, when the nano-processing was performed, as compared with the mixer-processing, the methane conversion rate was significantly enhanced immediately after the start of the measurement. When the micro-processing was performed, as compared with the case where the mixer-processing was performed, the final methane conversion rate was satisfactory.

Figure 10:
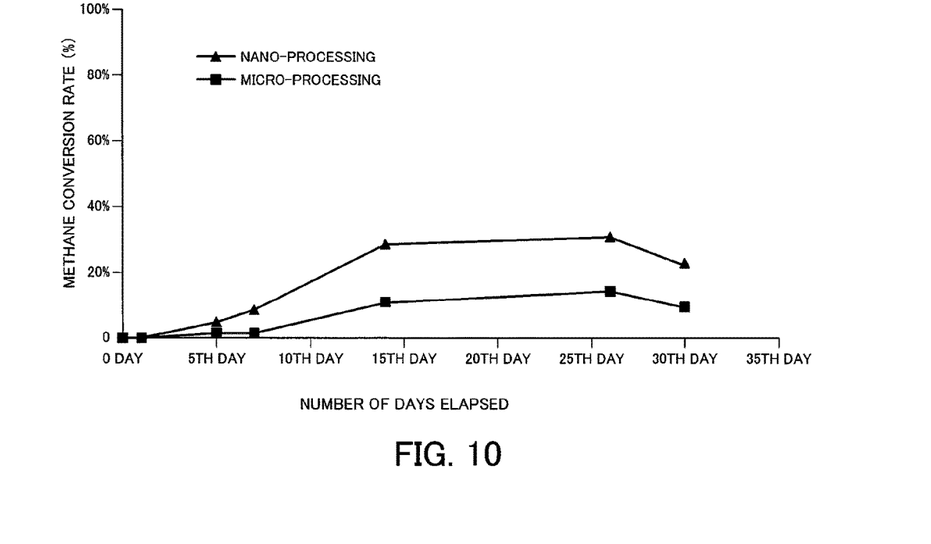
FIG. 10 is a graph showing the methane conversion rate in the Examples when palm is used as the organic substance.

Then, the results of the measurements when the palm was used as the organic substance are shown in Table 2, and the transition of the methane conversion rate in each of the samples is shown in FIG. 10. In addition, in a case where the palm was used as the organic substance, the measurements were performed only when the nano-processed products and the micro-processed products in the Examples were used.

TABLE 2

| Sample | Sludge | Water | Amount of sample | gCOD/TS | COD (mg/l) | TS (%) | Input amount (g) | Input amount (ml) | Input COD (g) | CH4max (ml) |
|---|---|---|---|---|---|---|---|---|---|---|
| Micro-processed 1 | 30 g | 9.0 g | 1.0 ml | — | 130,600 | — | — | 1.01 | 0.1319 | 50.39 |
| Micro-processed 2 | | | | — | 130,600 | — | — | 1.01 | 0.1319 | 50.39 |
| Micro-processed 3 | | | | — | 130,600 | — | — | 1.01 | 0.1319 | 50.39 |
| Nano-processed 1 | 30 g | 8.3 g | 1.7 ml | — | 78,067 | — | — | 1.69 | 0.1319 | 50.40 |
| Nano-processed 2 | | | | — | 78,067 | — | — | 1.69 | 0.1319 | 50.40 |
| Nano-processed 3 | | | | — | 78,067 | — | — | 1.69 | 0.1319 | 50.40 |

When the palm was used as the organic substance, as shown in Table 2, methane gas was generated in each of the nano-processing and the micro-processing.

Also, as shown in FIG. 10, when the nano-processing was performed, the methane conversion rate was enhanced whereas when the micro-processing was performed, the methane conversion rate was increased 10 days after the start of the measurement.

Figure 11:
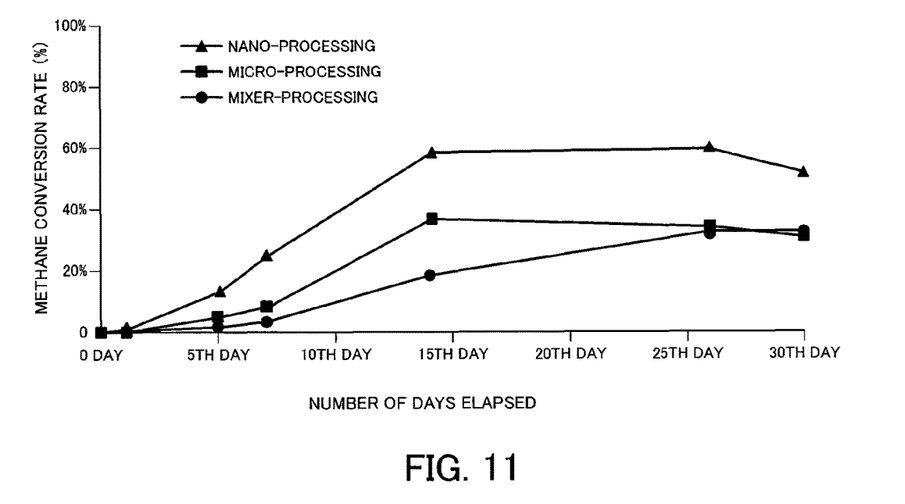
FIG. 11 is a graph showing the methane conversion rate in the Examples and the Comparative Example when coffee grounds are used as the organic substance.

Then, the results of the measurements when the coffee grounds were used as the organic substance are shown in Table 3, and the transition of the methane conversion rate in each of the samples is shown in FIG. 11.

TABLE 3

| Sample | Sludge | Water | Amount of sample | gCOD/TS | COD (mg/l) | TS (%) | Input amount (g) | Input amount (ml) | Input COD (g) | CH4max (ml) |
|---|---|---|---|---|---|---|---|---|---|---|
| Mixer-processed 1 | 30 g | 9.5 g | 0.5 g | — | 270,500 | — | — | 0.49 | 0.1325 | 50.64 |
| Mixer-processed 2 | | | | — | 270,500 | — | — | 0.49 | 0.1325 | 50.64 |
| Mixer-processed 3 | | | | — | 270,500 | — | — | 0.49 | 0.1325 | 50.64 |
| Micro-processed 1 | 30 g | 9.2 g | 0.8 ml | — | 174,267 | — | — | 0.76 | 0.1324 | 50.60 |
| Micro-processed 2 | | | | — | 174,267 | — | — | 0.76 | 0.1324 | 50.60 |
| Micro-processed 3 | | | | — | 174,267 | — | — | 0.76 | 0.1324 | 50.60 |
| Nano-processed 1 | 30 g | 8.4 g | 1.6 ml | — | 82,267 | — | — | 1.60 | 0.1316 | 50.29 |
| Nano-processed 2 | | | | — | 82,267 | — | — | 1.60 | 0.1316 | 50.29 |
| Nano-processed 3 | | | | — | 82,267 | — | — | 1.60 | 0.1316 | 50.29 |

When the coffee grounds were used as the organic substance, as shown in Table 3, methane gas was generated in each of the nano-processing, the micro-processing and the mixer-processing.

Also, as shown in FIG. 11, when the nano-processing was performed, as compared with the case where the mixer-processing was performed, the methane conversion rate was significantly enhanced immediately after the start of the measurement. When the micro-processing was performed, as compared with the case where the mixer-processing was performed, the methane conversion rate was enhanced 5 days after the start of the measurement.

The present invention is, for example, utilized for decomposing, with an anaerobic microorganism, an organic waste containing organic substances such as food residues, livestock manure and woody raw materials and thereby causing methane fermentation so as to generate useful methane gas.

The invention claimed is:

1. A methane fermentation system which decomposes an organic substance with an anaerobic microorganism to cause methane fermentation so as to generate methane gas, the methane fermentation system comprising:
   a wet bead mill which finely pulverizes the organic substance;
   a methane fermentation chamber in which the organic substance finely pulverized in the wet bead mill is decomposed with the anaerobic microorganism to cause the methane fermentation so as to generate the methane gas;
   an ultrafiltration (UF) membrane separator which concentrates and separates a digestive fluid after the methane fermentation in the methane fermentation chamber into a concentrated liquid and a permeation liquid; and
   a piping member returning the concentrated liquid to the methane fermentation chamber,
   wherein a water flow is produced within the methane fermentation chamber by separately returning the concentrated liquid directly to the methane fermentation chamber and contents of the methane fermentation chamber are agitated by the water flow.

2. The methane fermentation system according to claim 1, wherein the wet bead mill finely pulverizes the organic substance such that a particle diameter at 50% in a cumulative distribution with respect to a volume is equal to or less than 20 μm.

3. The methane fermentation system according to claim 1, further comprising:
   a reverse osmosis (RO) membrane separator which separates the permeation liquid.

4. The methane fermentation system according to claim 1, wherein the wet bead mill finely pulverizes the organic substance in which a moisture content of the organic substance is adjusted such that a solid content is equal to or less than 10%.

5. The methane fermentation system according to claim 1, further comprising:

a crusher crushing a colony of the anaerobic microorganism included in the digestive fluid after the methane fermentation in the methane fermentation chamber.

\* \* \* \* \*